United States Patent
Vereijken et al.

(10) Patent No.: US 8,594,946 B2
(45) Date of Patent: Nov. 26, 2013

(54) METHOD OF PERFORMING A BIOLOGICAL ASSAY

(75) Inventors: Adrianus Lambertus Johannus Vereijken, Boxmeer (NL); Annemieke Paula Jungerius, Rhenen (NL); Gerardus Antonius Arnoldus Albers, Boxmeer (NL)

(73) Assignee: Hendrix Genetics B.V., Boxmeer (NL)

( * ) Notice: Subject to any disclaimer, the term of this patent is extended or adjusted under 35 U.S.C. 154(b) by 44 days.

(21) Appl. No.: 12/447,860

(22) PCT Filed: Oct. 31, 2008

(86) PCT No.: PCT/NL2008/050687
§ 371 (c)(1),
(2), (4) Date: Mar. 24, 2010

(87) PCT Pub. No.: WO2009/058016
PCT Pub. Date: May 7, 2009

(65) Prior Publication Data
US 2010/0216666 A1     Aug. 26, 2010

(30) Foreign Application Priority Data
Oct. 31, 2007   (EP) ..................................... 07119761

(51) Int. Cl.
G01N 33/48   (2006.01)
G01N 31/00   (2006.01)
G06G 7/48    (2006.01)
G06G 7/58    (2006.01)

(52) U.S. Cl.
USPC .................... 702/19; 702/22; 703/11; 703/12

(58) Field of Classification Search
None
See application file for complete search history.

(56) References Cited

PUBLICATIONS

Wilkening et al. (BioTechniques, 2005, 39, 853-858).*
Flot et al., "Phase Determination from Direct Sequencing of Length-Variable DNA regions", Molecular Ecology Notes, vol. 6, pp. 627-630; 2006.
Muir et al., "Fitness Components and Ecological Risk of Transgenic Release: A Model Using Japanese Medaka (*Oryzias latipes*)", The American Naturalist, vol. 158:1, pp. 1-16; 2001.
Sunnucks et al., "SSCP is not so Difficult: The Application and Utility of Single-Stranded Conformation Polymorphism in Evolutionary Biology and Molecular Ecology", Molecular Ecology, vol. 9, pp. 1699-1710; 2000.
L.A. Knapp, "Denaturing Gradient Gel Electrophoresis and its Use in the Detection of Major Histocompatibility Complex Polymorphism", Tissue Antigens, vol. 65, pp. 211-219; 2005.
Ding et al., "Direct Molecular Haplotyping of Long-Range Genomic DNA with M1-PCR", PNAS, vol. 100:13, pp. 7449-7453; 2003.
Pettersson et al., "Molecular Haplotype Determination Using Allele-Specific PCR and Pyrosequencing Technology", Genomics, vol. 82, pp. 390-396; 2003.
van As et al., "Global Assessment of Chicken Variation Using the 18K Chicken SNP Iselect Infinium Assay"; 2008.
Assay Technology: Infinium Assay; http://www.illumina.com/pages.ilmn?ID=12.
Technology: Veracode Technology; http://www.illumina.com/pages.ilmn?ID=6.

* cited by examiner

*Primary Examiner* — Larry D Riggs, II
(74) *Attorney, Agent, or Firm* — Hoffmann & Baron, LLP

(57) ABSTRACT

The present invention relates to a method of pooling samples to be analyzed for a categorical variable, wherein the analysis involves a quantitative measurement of an analyte, said method of pooling samples comprising providing a pool of n samples wherein the amount of individual samples in the pool is such that the analytes in the samples are present in a molar ratio of $x^0 : x^1 : x^2 : x^{(n-1)}$, and wherein x is equal to a positive value other than 1 representing the pooling factor.

9 Claims, 6 Drawing Sheets

US 8,594,946 B2

METHOD OF PERFORMING A BIOLOGICAL ASSAY

FIELD OF THE INVENTION

The invention relates to the field of measurements with categorical outcome on biological samples, more in particular to methods for sample preparation of bioassays with categorical outcome. The present invention provides a method of pooling samples, the use of said method for genotyping an allelic variant. The invention further provides a method of performing an analysis on multiple samples, a pooling device for pooling multiple samples into a pooled sample, an analysis device comprising a processor that is arranged for performing an analysis on a set of pooled sample, a computer program product that puts into force a method of pooling samples, and a computer program product that puts into force a method for performing an analysis on multiple samples.

BACKGROUND OF THE INVENTION

A bioassay is a procedure where a property, concentration or presence of a biological analyte is measured in a sample. Bioassays are an intrinsic part of research in all fields of science, most notably in life sciences and especially in molecular biology.

A particular type of analysis in molecular biology relates to genotyping and sequencing. Genotyping and sequencing refers to the process of determining the genotype of an individual with a biological assay. Current methods include PCR, DNA and RNA sequencing, and hybridization to DNA and RNA microarrays mounted on various carriers such as glass plates or beads. The technology is intrinsic for test on father/motherhood, in clinical research for the investigation of disease-associated genes and in other research aimed at investigating the genetic control of properties of any species for instance whole genome scans for QTL's (Quantitative Trait Loci).

Due to current technological limitations, almost all genotyping is partial. That is, only a small fraction of an individual's genotype is determined. In many instances this is not a problem. For instance, when testing for father-/motherhood, only 10 to 20 genomic regions are investigated to determine relationship or lack thereof, which is a tiny fraction of the human genome.

Single nucleotide polymorphisms (SNPs) are the most abundant type of polymorphism in the genome. With the parallel developments of dense SNP marker maps and technologies for high-throughput SNP genotyping, SNPs have become the markers of choice for many genetic studies. A substantial number of samples is required in mapping and association studies or in genomic selection experiments.

In order to provide for high-throughput genotyping capabilities, arraying technologies have been developed. Such technologies are available from commercial suppliers such as Affymetrix (microarray-based GeneChip® Mapping arrays), Illumina (BeadArray™), Biotrove (Open Array™) and Sequenom (MassARRAY™). In many species (humans, livestock, plants, bacteria and viruses) a large number of SNPs is available or will become available in the near future. New innovations have enabled whole-genome genotyping or association studies and associated whole-genome selection programs for plant and animal breeding. Yet the costs of such programs are still significant, requiring budgets of up to several millions of dollars if samples are individually genotyped. Therefore, studies aimed at identifying SNPs in any species, currently involve analysis of only a limited number of individuals. The current invention therefore is of great significance since it allows a very substantial reduction of the cost of genotyping.

In order to obtain full insight in genomic variability it is necessary to know the full sequence of (a relevant part of) the genome. However, the cost of determining the full sequence is even higher than the cost of genotyping which is described in the previous paragraph. Despite the costs, it is expected that sequencing will replace genotyping to provide individual genotypes for the entire genome or specific regions thereof. The current invention also provides methods to reduce the cost of sequencing.

Sample pooling is regularly used in studies on categorical traits as a means to reduce analysis costs. The presence of the characteristic in the pool, consisting of a mixture of several samples indicates the presence of that characteristic in at least one of the samples in that pool. DNA pools are for instance used for:
  estimating allele frequencies in a population.
  By taking a good sample of individuals from the population, the raw allele frequency of allele 1 is calculated as the ratio between the result for allele 1 and the sum of the result for allele1 and the result for allele2 in the pool.
  case-control association studies wherein cases and controls are divided into separate pools, and
  reconstructing haplotypes on a limited number of individuals and a limited number of SNPs.
  Based on the allele frequencies measured in the pool, haplotypes can be estimated by different algorithms such as maximum likelihood. The term haplotype frequency is synonymous with the term joint distribution of markers.

An important disadvantage of sample pooling is that the measured characteristic is only identified in the pool as a whole, and not in any of the individual samples in the pool. One exception is DNA pools for genotyping trios (father, mother and child) when two pools each consisting of two individuals are created (father+child and mother+child). The observed allele frequency in each pool is indicative of the genotypes for all 3 individuals. This type of sample pooling provides a cost reduction of 33% but is only possible with such trios. In all other instances, pooled samples must be re-analysed individually in order to provide results for the individual samples.

Thus, it would be beneficial to provide sample pools for sample types other than trios, while still providing test results for the individual samples within that pool.

SUMMARY OF THE INVENTION

The present inventors have now discovered that random individuals can be pooled and that individual genotypes can be recovered from such pools when the contribution of each individual sample in the pool is a fixed proportion of that of each other sample, i.e. when sample amounts are not equimolar but provided in specific ratios. Results for individual samples can be inferred from the pooled test-result provided that the test involves a quantitative measure of a categorical variable, i.e. that the test involves a categorical or discrete trait that is quantitatively measured.

In fact, the present inventors have found that for the study of the presence of a certain allele at a certain locus in a diploid animal, the mixing in a ratio of 1:3 of a DNA sample of a first diploid animal having 2 possible alleles (A or B) at a single locus, with a DNA sample of a second diploid animal also having 2 possible alleles (A or B) at the same locus, results in the presence of (2)+(2+2+2)=8 possibilities for either of the alleles in that mixture, wherein the expected quantitative instrument signal from a single allele (e.g. A) is 12.5% of the maximum sample signal strength. This means that at a measured signal intensity of 37.5% of maximum sample signal strength, the sample comprises 3× the allele A, which means that the signal cannot be derived from the first diploid animal and can only be derived from the second diploid animal, indicating that the first diploid animal has genotype BB and the second diploid animal has genotype AB. Likewise, when the measured signal intensity is 50% of maximum sample signal strength, all samples have genotype AB. When the measured signal intensity is 0% of maximum sample signal strength, then all samples have genotype BB. The 2 individuals in the pool have in total 3*3 possible genotypes. Provided the accuracy of the measurement is at least 6.25%, each measurement can be allocated to a value one-eighth (⅛) of 100% or a multiple thereof. In general, each possible measurement result can be allocated to a value $1/(y*((p+1)^0+(p+1)^1+(p+1)^2+(p+1)^{(n-1)}))*100\%$, wherein y=2 (the two possible outcomes for allele A at one position, allele is present or absent), p is the ploidy level, n is the number of samples and 100% is the maximum sample signal strength. In total there will be (ploidy level+1)$^n$ possible genotypes.

Now when pooling samples of 3 animals (x, y and z) in a ratio of 1:3:9 (respectively, that is, with a pooling factor of 3), there are in theory a total of 26 possibilities for either of the alleles in that mixture, wherein the expected quantitative signal from a single allele (e.g. A) is 3.85% of the maximum sample signal strength. This means that at a measured signal intensity of 12% of maximum sample signal strength, the sample comprises 3× the allele A indicating that animal x has genotype BB, animal y has genotype AB, and animal z has genotype BB. Likewise, when the measured signal intensity is 96% of maximum sample signal strength, sample x has genotype AB, while samples y and z have genotype AA. Provided the accuracy of the measurement is at least 1.9%, each measurement can be allocated to a value one-twentysixth (1/26) of 100% or a multiple thereof. (For an overview of possible outcomes for such a pooled experiment see the Examples below).

The inventors have shown that this principle can be used for a large number of analyses involving a quantitative measurement of an analyte in a sample, wherein the result of the analysis is categorical with respect to a quality of the analyte in said sample.

In a first aspect, the present invention now provides a method of pooling samples to be analyzed for a categorical variable, wherein the analysis involves a quantitative measurement of an analyte, said method of pooling samples comprising providing a pool of n samples wherein the amount of individual samples in the pool is such that the analytes in the samples are present in a molar ratio of $x^0:x^1:x^2:x^{(n-1)}$, and wherein x is an integer of 2 or higher, such as 3, 4, 5, 6, 7, or 8, preferably 2 or 3, representing the number of classes of the categorical variable (or the pooling factor) and n is the number of samples. The annotation $x^0:x^1:x^2:x^{(n-1)}$ should be understood as referring to $x^0:x^1:x^2:\ldots:x^{(n-1)}$, or $x^0:x^1:x^2:x^{(n-1)}$, wherein n is the number of samples and i is an incremental integer having a value between 2 and n.

For pooling polyploid individuals x is equal to the (ploidy level+1), so x=2 for a haploid, 3 for a diploid and 5 for a tetraploid individual with two possible alleles at one single position, x is also equal to the number of possible genotypes.

Assume there would be three possible alleles then a haploid would have 3 possible genotypes (x=3), a diploid would have 6 possible genotypes (x=6) and a triploid would have 10 possible genotypes (x=10). In one diploid individual the first allele can occur 0, 1 or 2 times just as the second and third allele. This makes it possible to pool in the same ratio ($x^0:x^1:x^2:x^{(n-1)}$) as with two alleles (x is again polyploidy level+1). Signal intensities for the 3 alleles are rounded to the nearest result point $(1/(y*((p+1)^0+(p+1)^1+(p+1)^2+(p+1)^{(1-1)}))*100\%$, where y=2 (allele 1, 2 or 3 is present or absent), p=ploidy level and n=number of samples) to find the number of alleles in the pooled sample.

Thus, the ratio between the two individual samples in the pool (as an example) is such that the analytes therein are present in a molar ratio of 1:x wherein x is the maximum number of classes for the categorical trait.

Methods wherein the amount of the individual samples in the pool is provided as geometric sequence with common ratio 3 are particularly suitable for genotyping an allelic variant in diploid individuals, wherein each individual has three possible genotypes. The genotype is the categorical trait which may have three possible variants (AA, AB and BB).

Methods wherein the amount of the individual samples in the pool is provided as geometric sequence with common ratio 2 are particularly suitable for genotyping an allelic variant in haploid individuals. For an example thereof, reference is made to the experimental part below.

In another aspect, the present invention relates to the use of a method of the invention as described above, for genotyping an allelic variant in haploid or polyploid individuals wherein the number of classes of the categorical variable (x) equals p+1, wherein p represents the ploidy level of said individual. Such use for instance allows for genotyping an allelic variant in a diploid or haploid individual.

In yet another aspect, the present invention relates to a method of performing an analysis on multiple samples, comprising pooling said samples according to a method of the invention as described above to provide a pooled sample and performing said analysis on said pooled sample. The quantitative result obtained is then rounded off to the nearest result point (determined by the number of theoretical intervals in which maximum sample signal strength is divided for each possible result, see infra), and the signal intensity is allocated to the total number of classes of the categorical variable in the pooled sample. From this the categorical variable is determined for each individual sample in the pool taking into account the ratio of the various individual samples in the pool.

In another aspect, the present invention provides a method of performing an analysis on multiple samples, comprising performing an analysis on a set of pooled sample obtained by a method of pooling samples as defined herein above, wherein said sample is analyzed for a categorical variable and involves a quantitative measurement of an analyte in said sample.

In a preferred embodiment of this method, a method of performing an analysis further comprises the step of deducing from the measurement the contribution of the individual samples in said pool of samples.

In another aspect, the present invention provides a pooling device for pooling multiple samples into a pooled sample comprising a sample aspirator for providing a pooled sample and further comprising a processor for performing a method of pooling samples as defined herein above.

In another aspect, the present invention provides an analysis device comprising a processor that is arranged for performing an analysis on a set of pooled sample obtained by a method of pooling samples as defined herein above, wherein said device is arranged for analysing said sample for a categorical variable and for performing a quantitative measurement of an analyte in said sample.

In a preferred embodiment of this analysis device, the device further comprises a pooling device, most preferably a pooling device as disclosed above.

In another aspect, the present invention provides a computer program product either on its own or on a carrier, which program product, when loaded and executed in a computer, a programmed computer network or other programmable apparatus, puts into force a method of pooling samples as defined herein above.

In another aspect, the present invention provides a computer program product either on its own or on a carrier, which program product, when loaded and executed in a computer, a programmed computer network or other programmable apparatus, puts into force a method for performing an analysis on multiple samples, said method comprising performing an analysis on a set of pooled sample obtained by a method of pooling samples as defined herein above, wherein said sample is analyzed for a categorical variable and involves a quantitative measurement of an analyte in said sample.

In a preferred embodiment of this computer program product, the said method further comprises the step of pooling according to a method of pooling samples as defined herein above.

By using the method of the present invention analysis costs can be reduced immensely, i.e. typically by 50%, and even by 66% or more.

DESCRIPTION OF THE PREFERRED EMBODIMENTS

The term "categorical variable", as used herein, refers to a discrete variable such as a characteristic or trait, e.g. the presence or absence of an analyte or a characteristic therein, or an allelic trait present or absent in homozygous or heterozygous form in an analyte. Discrete is synonymous for categorical and refers to non-linear or discontinuous. A "variable" generally refers to a (categorical) trait measuring a property of a sample. A categorical variable can be binary (consisting of 2 classes). A "class" refers to a group or category to which a measurement can be assigned. Thus, a purely categorical variable is one that will allow the assignment of categories and categorical variables take a value that is one of several possible categories (classes). In particular, the categorical variable may relate to the presence of a genetic marker such as a single nucleotide polymorphism (SNP) or any other genetic marker, an allele, an immune response, a disease, a resistance capacity, hair color, gender, status of disease infection, genotype or any other trait or property of a sample or biological entity. Although they can be measured numerically, for instance as a generated analyte-signal that can be received, read and/or recorded by an analysis device, categorical variables themselves have no numerical meaning and the categories have no intrinsic ordering. For example, gender is a categorical variable having two categories (male and female often coded as 0 and 1) and represent preferably unordered categories. Genotype is also a categorical variable having a number of preferably unordered categories (AA, Aa and aa sometimes coded as 2, 1 and 0).

The sample in aspects of the present invention may be any sample wherein a categorical variable is to be measured. The sample may be a biological sample such as a tissue or body fluid sample of an animal (including a human) or a plant, an environmental sample such as a soil, air or water sample. The sample may be (partially) purified or may be an untreated (raw) sample. The sample is preferably a nucleic acid sample, for instance a DNA sample.

The analyte whose presence or form is measured in a quantitative test may be any chemical or biological entity. In preferred embodiments, the analyte is a biomolecule and the categorical variable is a variant of said biomolecule. Preferably, the biomolecule is a nucleic acid, in particular a polynucleotide, such as RNA, DNA and the variant may for instance be a nucleotide polymorphism in said polynucleotide, e.g. an allelic variant, most preferably an SNP, or the base identity of a particular nucleotide position.

The analyte as defined herein can thus be a DNA molecule exhibiting a certain categorical variable (e.g. the base identity of a particular nucleotide position in that nucleic acid molecule, having a categorical value of A, T, C or G). The base identity of a particular nucleotide position can be measured by using a quantitative test, for instance based on fluorescence derived from a cDNA copy incorporating a fluorescent analogue of said nucleotide, such as known in the art of DNA sequencing. The quantitative level of the fluorescence emitted by said analogue in a particular position of the DNA and measured by an analysis device, is then assigned to a categorical value for that nucleotide position, e.g. as an Adenine for that position.

In determining the base identity of a particular nucleotide position, the invention pertains to pooling of individual samples of which the nucleotide sequence of a particular nucleic acid is to be determined. The suitability of the method of the invention for sequencing assays (analyses) can be understood when realizing that sequencing assays involve the determination of a signal from either one of four possible bases wherein the presence or absence of a signal for any particular base at a certain position in for instance a sequencing gel corresponds to the presence or absence of that base identity in a particular nucleotide position within said nucleic acid. Pooling of two samples before running the sequence gel in the ratio as described herein will allow determination of the origin of any particular signal and thus of the sequence for each individual nucleic acid.

The "analyte" may be a polypeptide, such as a protein, a peptide or an amino acid. The analyte may also be a nucleic acid, a nucleic acid probe, an antibody, an antigen, a receptor, a hapten, and a ligand for a receptor or fragments thereof, a (fluorescent) label, a chromogen, radioisotope. Fact, the analyte can be formed by any chemical or physical substance that can be measured quantitatively, and that can be used to determine the class of the categorical variable.

The term "nucleotide", as used herein, refers to a compound comprising a purine (adenine or guanine) or pyrimidine (thymine, cytosine or uracyl) base linked to the C-1-carbon of a sugar, typically ribose (RNA) or deoxyribose (DNA), and further comprising one or more phosphate groups linked to the C-5-carbon of the sugar. The term includes reference to the individual building blocks of a nucleic acid or polynucleotide wherein sugar units of individual nucleotides are linked via a phosphodiester bridge to form a sugar phosphate backbone with pending purine or pyrimidine bases.

The term "nucleic acid" as used herein, includes reference to a deoxyribonucleotide or ribonucleotide polymer, i.e. a polynucleotide, in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

The term "quantitative measurement" refers to the determination of the amount of an analyte in a sample. The term "quantitative" refers to the fact that the measurement can be expressed in numerical values. The numerical value may relate to a dimension, size, extent, amount, capacity, concentration, height, depth, width, breadth, length, weight, volume or area. The quantitative measurement may involve the intensity, peak height or peak surface of a measurement signal, such as a chromogenic or fluorescence signal, or any other quantitative signal. In general, when determining the presence or form of an analyte, the measurement will involve an instrument signal. For instance, when determining the presence of an SNP, the measurement will involve a hybridization signal, and the measurement will typically provide a fluorescence intensity as measured by a fluorimeter. When determining the presence of an immune response, the measurement will involve measurement of an antibody titer and the measurement may also be typically provided as a fluorescence intensity. The measurement need not provide a continuous measurement result, but may relate to discrete intervals or categories. The measurement may also be semi-quantitative. As long as a the measurement can be determined in $2^{n-1}$, $3^{n-1}$ or $x^{n-1}$ partial and preferably proportional intervals of the maximum sample signal strength (depending on whether the pool is provided as geometric sequence with common ratio 2, 3 or x, respectively, wherein n is the number of samples in the pool), the measurement is in principle suitable.

The term "pooling", as used herein, refers to the grouping together or merging of samples for the purposes of maximizing advantage to the users. In particular the term "pooling" refers to the preparation of a collection of multiple samples to represent one sample of weighted value. Merging of multiple samples into one single sample is usually performed by mixing samples. In the present invention, mixing requires a careful weighing of the amount of the individual samples, wherein the amount of analyte present in each sample is decisive. When a sample A has an amount of analyte of 2 g/l and sample B has an amount of 1 g/l, these samples have to be pooled in a volume ratio of 1:6 in order to provide the 1:3 analyte ratio.

When two samples are e.g. pooled in a ratio of 1:3 or when three samples are pooled in a ratio of 1:3:9 as prescribed in embodiments of the present invention, the possible frequencies of the variants in the pools is set by the endpoints of intervals of 12.5% and 3.85%, respectively. The endpoints of these intervals are referred to herein as the "result points" and are equivalent to the step increments of the quantitative measurement up to reaching maximum sample signal strength.

The term "geometric sequence" refers to a sequence of numbers in which the ratio between any two consecutive terms is the same. In other words, the next term in the sequence is obtained by multiplying the previous term by the same number each time. This fixed number is called the common ratio for the sequence. In a geometric sequence of the present invention, the first term is 1 and the common ratio is 2 or 3, depending on the sample type.

The term "maximum sample signal strength" refers to the signal obtained from the pool when all samples in that pool provide a positive signal, i.e. when 100% of the individual samples are positive for the tested analyte. The maximum sample signal strength can be determined by any suitable method. For instance, 50 individual samples can be measured separately to determine their composition in terms of the number of discrete events present among these samples, and subsequently these samples may then be measured in a pooled experiment, wherein the signal strengths measured for the pooled sample are showing in the same proportion that would be obtained by adding up all signal strengths of all individual samples.

A method of the present invention may be performed with any number of n samples. However, in practice, the maximum number for n is set by the accuracy of the measurement method, i.e. the accuracy with which a statistically sound distinction between two consecutive result points can be determined. The accuracy (standard deviation) of the method must be in accordance therewith.

Applications of the method of the present invention include, but are not limited to, genotyping methods. Genotyping based on pooling of DNA has many applications. Genotypes can be used for mapping, association and diagnostics in all species. Specific genotyping examples include a) genotyping in humans, such as medical diagnostics but also follow-up individual typings following case-control study poolings; b) genotyping in livestock, such as individual typings in QTL studies, in candidate gene approaches and in genome wide selection applications, and c) genotyping in plants e.g. for mapping and association studies.

Pooling can also be used when sequencing humans, livestock, plants, bacteria, viruses. More specifically pooling of individual samples for sequencing is relevant when sequences of two or more individuals are to be compared.

A method of the present invention for pooling samples comprises the taking of a subsample from at least a first sample and a subsample from at least a second sample, wherein said first and second subsample are merged into a single container as to provide a mixture of the two subsamples in the form of a pooled sample and wherein the ratio of said first and second subsamples in said pooled sample is 1:3 or 3:1 based on the analyte concentration therein as described herein. Similarly, when three samples are pooled (which phrasing refers to the fact that three subsamples are mixed) the ratio between the first, second and third subsample (in any order) to be obtained in the pooled sample is 1:3:9 as prescribed herein. The possible frequencies of the variants in the pools is set by the endpoints of intervals of 12.5% and 3.85%, respectively. The endpoints of these intervals are referred to herein as the "result points" and are equivalent to the step increments up to reaching maximum sample signal strength.

A method of pooling as defined herein may be performed by (using) a pooling device. Such a device suitably comprises a sample collector arranged for collecting and delivering a defined amount of sample, for instance in the form of a defined (but variable) volume. A suitable sample collector is a pipettor such as generally applied in robotic sample delivery and processing systems used in laboratories. Such robotics systems are usually bench-top apparatuses, suitably comprising one or more of a microplate processor stages, reagent stations, filter plate aspirators, and robotic pipetting modules based on pneumatics and disposable pipette tips. These sample robot systems are very suitable for performing the method of the present invention as they are ultimately designed to combine different liquid volumes from different samples into one or more reaction tubes. Therefore, it is within the level of skill of the artisan to adapt such a pipetting robotic system to perform the task of combining different liquid volumes from different samples into a single pooled sample. Such a pipetting robotic system is however only one suitable embodiment of a sample pooling device for of pooling multiple samples into a pooled sample, said device comprising a sample collector for collecting samples from multiple sample vials and for delivery of samples into a single pooling vial to provide a pooled sample, and further comprising a processor that is arranged for performing a method of pooling samples as defined herein. The term "processor", as used herein, is intended to include reference to any computing device in which instructions stored and retrieved from a memory or other storage device are executed using one or more execution units, such as a unit comprising a pipetting device and a robotics arm for moving said pipetting device between sample vials and pooling vials of a pipetting robotic system. The term vial should be interpreted broadly and may include reference to an analysis spot on an array. Processors in accordance with the invention may therefore include, for example, personal computers, mainframe computers, network computers, workstations, servers, microprocessors, DSPs, application-specific integrated circuits (ASICs), as well as portions and combinations of these and other types of data processors. Said processor is arranged for receiving instructions from a computer program that puts into force a method of pooling samples according to the present invention on a pooling device as defined herein above.

A method of pooling samples to be analyzed for a categorical variable, wherein the analysis involves a quantitative measurement of an analyte, said method of pooling samples comprising providing a pool of n samples wherein the amount of individual samples in the pool is such that the analytes in the samples are present in a molar ratio of $x^0:x^1:x^2:x^{(n-1)}$, and wherein x is an integer of 2 or higher representing the number of classes of the categorical variable While the method of pooling is quite straightforward, and can be described in terms of relatively simple formula's, the method of analysis of pooled samples as described herein is more intricate.

As described herein, a categorical variable (e.g. genotype) may take a value that is one of several possible categories (BB, AB, AA). These categories coincide with classes of result intervals. The categories are determined by performing a quantitative measurement on an analyte (DNA) for a parameter (e.g. fluorescence), and assigning classes to these parameter values based on categorization of analysis results, each of which classes represents a variant for said categorical variable (See FIG. 7).

In general, the total number of possible analysis results (outcomes) depends on the nature of the categorical variable. For instance in the case of a genotype of a diploid organism, the ploidy level determines the number of possible analysis results. In general terms, the nature of the categorical variable can include the presence of different numbers of variants or sets of the analyte (repeats in FIG. 7) within a sample. Also, the total number of possible analysis results depends on the possible different categorical values one repeat can take. An example of the number of possible analysis results is provided in Table 1.

TABLE 1

Total number of possible analysis results (outcomes) for a measurement when this is composed of repeats of the same event.

| Possible values for | Number of repeats within a sample | | | |
| --- | --- | --- | --- | --- |
| 1 repeat | 1 | 2 | 3 | 4 |
| 2 | 2 | 3 | 4 | 5 |
| 3 | 3 | 6 | 10 | 15 |
| 4 | 4 | 10 | — | — |
| 5 | 5 | 15 | — | $(^{n+}k^{k+1})$ |

N represents the number of possible categorical values or variants for one repeat and k is the number of repeats within the sample. The values provided in the table are calculated based on the formula $(^{n+}k^{k+1})$.

For instance, the genotype of a diploid individual (2 repeats of one allele within one sample) is equal to 3 (AA, AB and BB) because one allele can have only two different variants (A or B). A triploid (3 repeats of one allele) can have 4 different genotypes (AAA, AAB, ABB and BBB).

A blood group for an individual is one repeat having four different variants (A, B, AB or O).

The formula in table 1 holds for situations were it is not important for which repeat the variant is measured. For instance for genotyping there is no difference between genotype AB and genotype BA. However, in case the identity of the repeat is important then the formula fopr calculating the total number of possible analysis results is $n^k$. This formula then replaces the formula $(^{n+}k^{k+1})$ in Table 1. Also all values in the table change accordingly. For a situation with 2 repeats and 2 possible results for a repeat there will be 4 results. With 3 repeats and 3 possible results for a repeat there will be 9 different results.

The total number of possible analysis results is applied herein as pooling ratio (e.g. 1:3:9) and directly provides what is called the "pooling factor" (3 in the case of 1:3:9). For instance when pooling haploid individuals for genotyping there is one repeat having 2 possible variants per repeat. In such cases the pooling factor is equal to 2 (is number of results in table 1).

Pooling 4 individuals then need to be done in the ratio $2^0:2^1:2^2:2^3$.

When pooling diploid individuals the pooling factor is 3. Pooling 3 individuals need to be done in the ratio $3^0:3^1:3^2$.

The total number of results in a pool then is equal to following formula;

Total pool results=pooling factor$^{number\ of\ samples}$.

The increment for the signal intensities is then equal to;

Increment=1/(pooling factor$^{number\ of\ samples}$−1)*100% or

1/(y*((pooling factor)$^0$+(pooling factor)$^1$+(pooling factor)$^2$+ . . . +(pooling factor)$^{(n-1)}$))*100%, where n is the number of samples and y=pooling factor minus 1.

If measurement intensities are present for all variants for one repeat (are all values minus one because the missing one can then be calculated as 1 minus intensities for the other) the top row in Table 1 is followed because this can be seen as present or absent for every value of that repeat which corresponds to 2 possible outcomes for this repeat. See example above where 3 possible alleles are assumed instead of 2 and where one can measure 3 different light intensities in stead of 2 (red and green).

If there is only a single measurement table 1 can be followed.

A method of the present invention for analysing pooled samples as contemplated herein comprises the performance of a measurement for the required analyte on said pooled sample. Upon recording of a measurement result, for instance an instrument signal, the analysis then involves a series of steps that is exemplified in great detail in the Examples provided herein below.

Performing an analysis on a set of pooled sample obtained by a method of the invention wherein said sample is analyzed for a categorical variable, involves a quantitative measurement of an analyte in said sample. The analyte is a chemical or physical substance or entity a parameter of which is indicative for the presence or absence of at least one variant of said categorical variable. For instance, when determining as a categorical variable the genotype of an organism, having variant alleles A or B, the analyte is the organism's DNA, a DNA probe or a genetic label and the absolute value of a parameter of that analyte may be correlated directly to the presence (or absence) of the variant. The quantitative measurement for the analyte will generally involve a fluorescence intensity, a radioisotope intensity, or any quantitative measurement as a value for the analyte parameter. Measurement values beyond a certain threshold or categorical value will generally indicate the presence of the variant. Quantitative measurement of an analyte in a sample thus refers to an analyte signalling the presence or absence of a variant of that categorical variable which is to be analyzed in said sample.

Essentially, in a method of analysing a pooled sampled obtained by a method of pooling samples as described herein, the contribution of the individual samples in said pool, that is, the result for the individual samples in the pool, is determined as follows.

First the maximum sample signal strength for a certain analysis "A" to be performed on a pool of n samples is determined and set at 100% signal. The maximum sample signal strength is the signal strength that is attained when 100% of the samples in a pool of n samples is positive for the categorical variable. The maximum sample signal strength can be determined by providing a test-pool of n positive reference samples and determining the measurement signal, wherein said positive reference samples are positive with regard to the categorical variable, and wherein n is the number of samples in the pools on which analysis "A" is performed. The maximum sample signal strength for analysis "A" is recorded or stored in computer memory for later use. Next, the analyte of interest is measured in a pooled sample obtained by a method of the present invention by performing analysis "A", whereby the signal strength of the pooled sample for the analyte is determined. The resulting signal strength for the analyte in the pooled sample is recorded, rounded off to the nearest result point as defined above and optionally stored, and then compared to the maximum signal strength. Suitably, this comparison can be performed as follows. In general, each possible measurement result can be allocated to a value $1/(y*(3^0+3^1+3^2+3^{(n-1)}))*100\%$, wherein n is the number of pooled samples, y is an integer of 2 representing "A" is present or absent and 100% is the maximum sample signal strength. The annotation $y*(3^0+3^1+3^2+3^{(n-1)})$ should be understood as referring to $y*(3^0+3^1+3^2+3^i+3^{(n-1)})$, wherein n is the number of samples and i is an incremental integer having a value between 2 and n. For instance for y=2 classes of a categorical variable (marker absent and marker present), and a pool of 4 samples, with the maximum sample signal strength set at 100% using 4 positive reference samples, there are in total $2*(3^0+3^1+3^2+3^3)=2+6+18+54=80$ result points, wherein each possible measurement result can be allocated to a value $1/80*100\%=1.25\%$ or a multiple thereof.

The result for each sample in a pool of samples can be read from a simple result table, which can be stored in computer readable form in a computer memory, and which table allocates for each result point of incremental steps of $1/(y*(3^0+3^1+3^2+3^{(n-1)}))*100\%$ between 0% and 100% of the maximum sample signal strength the corresponding value for each individual sample in the pool. For instance such a result table is the table as provided in Table 2 below.

The analysis is completed by assigning to each of the various subsamples in said pooled sample the categorical variable.

A method of analysing a pooled sample as defined herein may be performed by an analysis device. An analysis device of the present invention comprises a processor that is arranged for performing an analysis on a set of pooled sample obtained by a method for pooling samples as described above, wherein said device is arranged for analysing said sample for a categorical variable and for performing a quantitative measurement of an analyte in said sample. As noted above, the unique feature of the analysis device is that it is arranged for analysing a pooled sample for a categorical variable in each individual sample in said pool and for performing a quantitative measurement of an analyte in said sample. Essentially, the analysis device is arranged for measuring and analysing the measurement result obtained for the pooled sample and inferring from that result the categorical variable in each individual sample in a pool. Such a device suitably comprises a signal-reading unit for measurement of the analyte signal in the pooled sample. The analysis device further suitably comprises a memory for storing the measurement result and the result table as described above. The analysis device further suitably comprises a processor arranged for retrieving data from memory and/or from the reading unit, and arranged for performing a calculation and for performing an iterative process wherein the measurement result for the pooled sample are compared with and allocated to the corresponding results for the individual samples in said pool using the above referred result table; an input/output interface for entering sample data into the memory or processor; and a display connected to said processor. The processor is arranged for receiving instructions from a computer program that puts into force a method of analysing samples according to the present invention on an analysis device as defined herein above. The term "processor" as used herein is intended to include reference to any computing device in which instructions retrieved from a memory or other storage device are executed using one or more execution units, such as a signal reading unit for receiving a pooled sample and for performing the measurement of an analyte by determining the signal of said analyte in a sample or a pooled sample.

An analysis device of the present invention may further including the pooling device of the invention.

The invention further provides a computer program product either on its own or on a carrier, which program product, when loaded and executed in a computer, a programmed computer network or other programmable apparatus, puts into force a method of pooling samples as described above. Essentially, the computer program product may be stored in the memory of the pooling device of the invention and may be executed by a processor of said device by providing said processor with a set of instructions corresponding to the various process steps of the method of pooling.

The invention further provides a computer program product either on its own or on a carrier, which program product, when loaded and executed in a computer, a programmed computer network or other programmable apparatus, puts into force a method for performing an analysis on multiple samples, said method comprising performing an analysis on a set of pooled sample obtained by a method of pooling samples as described above, wherein said sample is analyzed for a categorical variable and involves a quantitative measurement of an analyte in said sample. Essentially, the computer program product may be stored in the memory of the analysis device of the invention and may be executed by a processor of said device by providing said processor with a set of instructions corresponding to the various process steps of the method of analysis. In the computer program product for performing an analysis, the method embedded in the software instructions may further comprises the step of pooling samples as described above.

The present invention will now be illustrated by way of the following non limiting examples.

EXAMPLES

Example 1

Example of Genotyping of Diploid Individual Samples for the Presence of SNPs Using 1 Pool of 50 Individuals for Standardization

Step 1) 50 individuals were tested separately.

For every SNP and every individual we obtained an intensity for red fluorescence (presence of allele) and green fluorescence (absence of allele) using two different fluorochromes in a microarray format. The ratio between red and green intensities is not always 1 (or 0) for a homozygous animal or 0.5 for a heterozygous animal.

The data on individual typings were used to calculate the correction factors from the signal intensities for all typed SNPs.

To obtain the most important correction factor (K), a correction factor often used to correct the data for any unequal efficiencies in representing the alleles, we used signals from heterozygous genotypes. If heterozygous genotypes were not present, we assumed that the SNP studied is not segregating in the population under research and therefore results for this SNP in the pools should be omitted.

Omission of SNPs due to absence of heterozygotes in the sample of 50 individuals may have as a consequence that information on SNP's with low MAF (minor allele frequency) could be lost. For many applications (such as genome wide selection) this is not harmful because SNPs with very low minor allele frequencies do not contribute very much to the accuracy and a decision then can be made not to use data on these SNPs or not to apply the correction factor.

The first correction factor (K) we used was;

$$K = \text{avg}(X_{raw}/Y_{raw})$$

wherein $X_{raw}$ is the measured intensity for red, and $Y_{raw}$ is the measured intensity for green. This value was determined from the individually genotyped samples with genotype AB.

In stead of using the average result of all beads for one genotype we also can use the results of all the separate beads. So from one sample we use the average result for Xraw and Yraw or for X and Y or we use the results of all separate beads from that sample.

The other correction factors were AAavg and BBavg. AAavg is the average of the uncorrected allele frequencies of AA genotypes. This value is expected to be close to 1. BBavg is the average of the uncorrected allele frequencies of BB genotypes. This value is expected to be close to 0. AAavg and BBavg were calculated using the formulas:

$$AAavg = (\text{avg}(X_{raw}/(X_{raw}+Y_{raw})))$$

and $$BBavg = (\text{avg}(X_{raw}/(X_{raw}+Y_{raw})))$$

Step 2) One testpool was constructed including all 50 individuals from step 1 above. To this end DNA concentration in ng/µl was measured in each individual sample using a NanoDrop spectrophotometer (NanoDrop Technologies, USA). All DNA samples were then diluted to a standard concentration of 50 ng/µl before pooling into a single sample. In the testpool thus obtained we estimated allele frequencies either uncorrected or based on the correction factors found in the first step.

Uncorrected allele frequency for allele A is calculated as a ratio between red intensity divided by the sum of both intensities as follows:

$$\text{Uncorrected allele frequency} = X_{raw}/(X_{raw}+Y_{raw})$$

The first correction for allele frequency we applied was $$\text{Corrected allele frequency} = X_{raw}/(X_{raw}+K^*Y_{raw})$$

The second correction we applied was a normalization.

$$\text{Normalized allele frequency} = (\text{Corrected allele frequency} - BBavg)/AAavg$$

For both correction and normalization we used all 3 genotypes for every SNP separately from the individual samples.

The order of accuracy of estimated allele frequencies was: normalized (most accurate), corrected (in between) and uncorrected (least accurate).

This means that if there were no heterozygous individuals in step 1 the correction factor K was set at 0.5, and if there were no homozygous individuals the correction factors AAavg and BBavg were set at 1 and 0, respectively.

Step 3) We compared allele frequencies calculated on individual typings and based on the results in the testpool. From this we estimated a fourth degree polynomial where the real results are on the X-axis. See FIG. 1 for a genotyping result in individuals tested separately and in pool with almost 18000 SNPs. Genotyping was done using the 18K Chicken SNP iSelect Infinium assay (Illumina Inc, USA), with SNPs evenly distributed throughout the chicken genome (van As et al., 2008). Details on the assay, workflow and chip can be found on the website of Illumina From this polynomial we calculated the predicted allele frequency in the testpool when the frequency known from individuals would be 0, 0.05, 0.1, 0.15 - - - 0.9, 0.95 and 1.

Putting these results in a second graph with the real frequencies on the Y-axis, we obtained correction factors for the third step of correction, see FIG. 2.

After applying these correction factors, the allele frequencies in the testpool showed a linear relation with the real frequencies, see FIG. 3.

In this experiment with about 18.000 SNP's over 96% of the allele frequencies measured in the testpool of 50 individuals (and corrected as described) were within the range of + or −6.25% compared to the results from individual typings.

For application of the invention, the previous 3 steps are preferably performed prior to the actual analysis as a "calibration" in order to enhance accuracy of the analysis. These steps need however not be performed each time. The calibration of the measurements (if performed) is then to be followed up by:

Step 4) Construct DNA pools of 2, 3 or n individuals in the ratio 1:3, 1:3:9 or $1:3^1:3^2:3^{(n-1)}$, and subject the pools to the measurement for genotyping, wherein signal intensities are determined for red and green on a microarray using the 18K Chicken SNP iSelect Infinium assay (vide supra).

Step 5) With the correction factors found in step 1 and step 3 the allele frequencies can be calculated from the resulting signal intensities in the pool. With two individuals in a pool the predicted corrected frequencies give the result points 0%, 12.5%, 25.0%, 37.5%, 50.0%, 62.5%, 75.0%, 87.5% and 100%. Rounding off should be done to the nearest result point. The genotypes of the two individuals can be derived from the results as indicated in Table 2.

With 3 individuals in a pool rounding off should be done to the nearest result point where intervals between result points are 3.85% ($100/(3^3-1)$) etc.

The shorter the intervals between the consecutive result points, the more accurate readings of intensities need to be in order to allow proper allocation of a particular result to one of the result points. More accurate readings will become feasible with further development of the genotyping technique.

For the situation with 2 individuals in a pool one can decide to use only the SNPs where the estimated and correct allele frequency in the pool falls within the ±6.25% range from the real frequency in the individuals (see red lines in FIG. 3).

TABLE 2

Result points of allele frequencies in pooled samples
and inferred genotypes of the two individuals in
the pool for a SNP with A and C allele

| Frequency of allele A in pooled sample | Inferred genotype of individual 1 (present in pool in 1 part) | Inferred genotype of individual 2 (present in pool in 3 parts) |
|---|---|---|
| 0 | CC | CC |
| 12.5 | AC | CC |
| 25 | AA | CC |
| 37.5 | CC | AC |
| 50 | AC | AC |
| 62.5 | AA | AC |
| 75 | CC | AA |
| 87.5 | AC | AA |
| 100 | AA | AA |

SNP's which show a larger difference than 6.25% between pooled results and individual results (in step 3) should be omitted if no other information is available to infer individual genotypes.

Additional information to infer individual genotypes may be derived from the pedigree of the individuals or from information on the haplotypes that are present in the family or the population to which the individual belongs.

Depending on the repeatability of the correction factors, step 1, 2 and 3 may be completely skipped in a new analysis where assay conditions are known to be the same.

When following the method of Example 1, significant savings can be obtained by reducing the total number of samples that need to be analysed whilst still obtaining reliable results on the original individual samples. Typical reductions of the total numbers of samples to be analysed are exemplified in Table 3.

TABLE 3

Savings in the number samples to be analysed when pooling 2 or 3 individuals following the method of the invention.

| Number of individuals to be genotyped | Number of samples when 2 individuals are pooled ||||  Number of samples when 3 individuals are pooled ||||
|---|---|---|---|---|---|---|---|---|
|  | Number of individuals plus pool | Number of pools of 2 individuals | Total number of samples | Reduction of number of samples to be analysed (%) | Number of individuals plus pool | Number of pools of 3 individuals | Total number of samples | Reduction of number of samples to be analysed (%) |
| 250 | 50 + 1 | 100 | 151 | 39.6 | 50 + 1 | 67 | 118 | 52.8 |
| 500 | 50 + 1 | 225 | 276 | 44.8 | 50 + 1 | 150 | 201 | 59.8 |
| 1000 | 50 + 1 | 475 | 526 | 47.4 | 50 + 1 | 317 | 368 | 63.2 |
| 2000 | 50 + 1 | 975 | 1026 | 48.7 | 50 + 1 | 650 | 701 | 64.9 |
| 5000 | 50 + 1 | 2475 | 2526 | 49.5 | 50 + 1 | 1650 | 1701 | 66.0 |

Example 2

Example of Genotyping of Diploid Individual Samples Using 25 Pools of 2 Individuals for Standardization Step 1) 50 individuals are tested separately as in step 1, example 1.

Step 2) Construct 25 pools of 2 samples each in the ratio 1:3 including all 50 individuals from step 1 above. In these pools estimate allele frequencies either uncorrected or based on the correction factors found in the first step.

Step 3) Compare the sum of the allele frequencies from the 2 individual typings and the estimated frequency in the pools of 2 individual samples. From these 25 points calculate a regression line. The regression coefficient and intercept can then be used to correct the estimated frequencies from other pools.

Step 4) Then construct DNA pools of 2, 3 or n individuals in the ratio 1:3, 1:3:9 or $1:3^1:3^2:3^{(n-1)}$.

Step 5) With the correction factors found in step 1 and step 3 calculate the allele frequencies from the resulting signal intensities in the pool.

The savings in sample numbers are identical to the savings mentioned in Table 8 for sequencing diploid individuals.

Example 3

Example of Genotyping of Haploid Individual Samples

When two haploid samples are pooled and measured for the presence of allele A at a certain position in the genome, the expected ratios in the measurements (peak height, surface under peak, intensities) are;

TABLE 4

Result points of allele frequencies in pooled samples
and inferred genotypes of the two individuals in
the pool for a SNP with A and C allele

| Frequency of allele A in pooled sample | Inferred genotype of individual 1 (present in pool in 1 part) | Inferred genotype of individual 2 (present in pool in 3 parts) |
|---|---|---|
| 0.00 | C | C |
| 0.33 | A | C |
| 0.67 | C | A |
| 1.00 | A | A |

If only pools of two samples are used correction factors may not be needed. When more samples are pooled correction factors probably are needed. They then can be calculated from pools of 2 samples with equal amounts of the analyte to simulate heterozygous and homozygous diploid individuals.

When pooling 3 samples are pooled in a ratio of 1:2:4, the following ratios in the measurements are expected;

TABLE 5

Result points of allele frequencies in pooled samples
and inferred genotypes of the three individuals
in the pool for a SNP with A and C allele

| Frequency of allele A in pooled sample | Inferred genotype of individual 1 (present in pool in 1 part) | Inferred genotype of individual 2 (present in pool in 2 parts) | Inferred genotype of individual 2 (present in pool in 4 parts) |
|---|---|---|---|
| 0.000 | C | C | C |
| 0.166 | A | C | C |

TABLE 5-continued

Result points of allele frequencies in pooled samples
and inferred genotypes of the three individuals
in the pool for a SNP with A and C allele

| Frequency of allele A in pooled sample | Inferred genotype of individual 1 (present in pool in 1 part) | Inferred genotype of individual 2 (present in pool in 2 parts) | Inferred genotype of individual 2 (present in pool in 4 parts) |
|---|---|---|---|
| 0.333 | C | A | C |
| 0.500 | C | C | A |
| 0.666 | A | C | A |
| 0.833 | C | A | A |
| 1.000 | A | A | A |

Example 4

Use of the Invention in Sequencing Protocols

The method of pooling described in this invention can be applied to situations were there is a need to determine sequences in 2 or more individuals.

Pooling of individuals, templates or PCR products for sequencing is not common practice because the essential problem when analyzing a double trace is that two bases are represented at each position and it is impossible to tell from which template each base came by exampling only the trace.

In addition to deliberately pooled templates resulting in double traces, several biological and biotechnical situations are known that give rise to double traces. These are seen in alternative spliced regions of a transcript that are amplified by RT-PCR, direct sequenced (without cloning) and random insertional mutagenesis experiments.

Several methods have been described to trace back the haplotypes of pooled sequences or double traces. Flot et al. 2006 describe several molecular methods that have been proposed to find out the haplotypes of an individual. E.g. sequencing cloned PCR products (e.g. Muir et al., 2001), SSCP (single stranded conformation polymorphism) (Sunnucks et al., 2000), denaturating gradient gel electrophoresis (DGGE) (Knapp 2005), extreme DNA dilution to single-molecule level (Ding & Cantor 2003) and the use of allele-specific PCR primers (Pettersson et al., 2003). In addition several computational methods have been purposed for haplotype reconstruction of mixtures of sequences.

All the described methods, however, can be very costly and time-consuming and are only applicable to specific purposes (e.g. resequencing, alternative splicing, templates or PCR amplified mixtures of two products that differ in sequence length, the availability of a reference genome sequence) and not for standard direct sequencing of haploid or diploid samples or de novo sequencing of completely unknown sequences.

The pooling of sequence templates following the pooling described in this invention can be applied to situations where the same sequence fragment can be obtained both in individuals and pooled samples. This means that e.g. shotgun sequencing (random sheared fragments) is not suitable for pooling.

In all applications mentioned above, if pooling is applied on purpose, equal amounts of template (samples, DNA, RNA or PCR product) are pooled. Herein we describe the pooling of unequal amounts of template. For this example only the situation for a pool consisting of 2 templates is described, but the invention can be used to construct pools of DNA (or post-PCR products) of 2, 3, or n individuals in the ratio 1:3, 1:3:9, $1:3^1:3^2:3^{(n-1)}$ for diploid organisms and in the ratio of 1:2, 1:2:4, $1:2^1:2^2:2^{(n-1)}$ for haploid organisms.

General conditions that need to be met are that the sequencing device scans templates (e.g. for fluorescence) and the resulting chromatogram represents the sequence of the DNA template as a string of peaks that are regularly spaced and of similar height.

Step 1) Perform sequence reactions for 50 individuals separately

The data on the individual sequencing reactions are used to calculate the correction factors from the peak areas or peak heights for all base (or nucleotide) positions.

Step 2) Perform sequence reactions for 25 pools of 2 pooled individuals

Peak area ratios are used to discriminate between first and second peak at base and noise peaks. The second peak is a percentage of the first peak and a threshold value is used to discriminate between peaks and noise peaks. The data on the pooled sequencing reactions are used to calculate the correction factors from the peak areas or peak heights for all base (or nucleotide) positions.

Step 3) Make a graph of the results of step 1 and 2 and construct the regression line (calculate regression coefficient and intercept).

Step 4) Construct pools of DNA (or post-PCR products)

Pools are constructed of 2, 3, or n individuals in the ratio 1:3, 1:3:9, $1:3^1:3^2:3^{(n-1)}$ for diploid organisms and in the ratio of 1:2, 1:2:4, $1:2^1:2^2:2^{(n-1)}$ for haploid organisms.

Step 5) With the correction factors found in step 1, 2 and step 3, the basecalling can be calculated from the resulting signal intensities in the pool In this example only 2 potential nucleotides (A and C) at each base position, are shown but the same principle works for other combinations of 2 out of the 4 available nucleotides that are basis of the genetic code. The average peak height for the "A" nucleotide is set to 100 and the average peak height of the "C" nucleotide is 75. Based on these peak heights, for every possible combination of nucleotides in the pool of two haploid samples the relative peak heights are presented in Table 6. The relative peak heights for a pool consisting of two diploid templates are given in Table 7.

TABLE 6

Result points of allele frequencies in pooled and
unpooled haploid individuals and inferred genotype
for a random position in the nucleotide sequence.

| Inferred genotype | | Peak area/height Unpooled | | Peak area/height Pooled (1:2 ratio) | |
|---|---|---|---|---|---|
| Individual 1 | Individual 2 | First peak (A) | Second peak (C) | First peak (A) | Second peak (C) |
| A |   | 100 |   |   |   |
| C |   |   | 75 |   |   |
| A | A |   |   | 100 |   |
| A | C |   |   | 33.3 | 50 |
| C | A |   |   | 66.6 | 25 |
| C | C |   |   |   | 100 |

TABLE 7

Result points of allele frequencies in pooled and unpooled diploid individuals and inferred genotype for a random position in the nucleotide sequence.

| Inferred genotype | | Peak area/height Unpooled | | Peak area/height Pooled (1:3 ratio) | |
|---|---|---|---|---|---|
| Individual 1 | Individual 2 | First peak (A) | Second peak (C) | First peak (A) | Second peak (C) |
| AA |    | 100 |       |      |        |
| AC |    | 50  | 37.5  |      |        |
| CC |    |     | 75    |      |        |
| AA | AA |     |       | 100  | 0      |
| AA | AC |     |       | 62.5 | 28.125 |
| AA | CC |     |       | 25   | 56.25  |
| AC | AA |     |       | 87.5 | 9.375  |
| AC | AC |     |       | 50   | 37.5   |
| AC | CC |     |       | 12.5 | 65.625 |
| CC | AA |     |       | 75   | 18.75  |
| CC | AC |     |       | 37.5 | 46.875 |
| CC | CC |     |       | 0    | 100    |

Table 8 indicates the reduction of the number of sequence reactions comparing the pooling strategy in this invention and the non-pooling situation.

TABLE 8

Savings in the number of samples or sequence reactions when pooling 2 individuals following the method of the invention.

| Number of individuals to be sequenced | Number of pools or samples to be sequenced using this invention | | | Reduction of number of samples to be sequenced (%) |
|---|---|---|---|---|
|  | Individuals + pools | Pools of 2 individuals | Total number of samples |  |
| 250  | 50 + 25 | 100  | 175  | 30%   |
| 500  | 50 + 25 | 225  | 300  | 40%   |
| 1000 | 50 + 25 | 475  | 550  | 45%   |
| 2000 | 50 + 25 | 975  | 1050 | 47.5% |
| 5000 | 50 + 25 | 2475 | 2250 | 49%   |

Example 5

Example of Genotyping of Diploid Individual Samples Using 1 Pool of 50 Individuals and 25 Pools of 2 Individuals for Standardization Using Alternative Correction Methods The Example Describes Several Experiments Step 1) 50 individuals were tested separately.
Same as in Example 1, Step 1 but with different correction method(s) using normalised intensities X and Y in stead of Xraw and Yraw.
The first correction factor (K) is calculated using X and Y.

$$K = avg(X/Y)$$

where X is the normalized intensity for the A allele (red) and Y is the normalized intensity for the B allele (green). This value was determined from the individually genotyped samples with genotype AB.

The other correction factors AAavg and BBavg are also based on X and Y. AAavg is the average of the uncorrected allele frequencies of AA genotypes. This value is expected to be close to 1. BBavg is the average of the uncorrected allele frequencies of BB genotypes. This value is expected to be close to 0. AAavg and BBavg were calculated using the formulas:

$$AAavg = (avg(X/(X+Y)))$$

and $$BBavg = (avg(X/(X+Y)))$$

All correction factors K, AAavg and BBavg can also be calculated based on Xraw and Yraw as in Example 1, Step 1.

If no genotypes AA are available among the 50 individuals AAavg is set to 1. Also if no BB genotypes are available then BBavg is set to 0.

Next step is to calculate allele frequencies based on the individual typings for those SNPs where all 50 individuals had a result.

Step 2) One pool was constructed including all 50 individuals from step 1 as in Example 1, Step 2.
Uncorrected allele frequency for allele A is calculated as a ratio between normalized red intensity (X) divided by the sum of both normalized intensities (X+Y)

$$\text{Uncorrected allele frequency} = X/(X+Y) \text{ (called Raf)}$$

The first correction for allele frequency we applied is $$\text{Corrected allele frequency} = X/(X+K*Y) \text{ (called Rafk)}$$

If there were no heterozygous genotypes, K can not be calculated. In that case following rules can be applied;
If Raf<0.1 then Rafk is set to 0.
If Raf 0.9 then Rafk is set to 1.
In all other situations were K is missing Rafk is set equal to Raf.

The normalisation correction using. AAavg and BBavg is not always needed when you start with the normalised intensities X and Y. If you start with Xraw and Yraw normalisation using AAavg and BBavg can be applied as in Example 1, Step 2.

If normalisation is applied then use the following formula;

$$\text{Normalized allele frequency} = (\text{Corrected allele frequency} - BBavg)/AAavg \text{ (called Rafn)}$$

Step 3) We compared the expected allele frequencies calculated on individual typings in step 1 and the observed (corrected or uncorrected) frequencies based on the results in the pool of 50 in Step 2. From this we calculated the regression coefficients using following model;

$$\text{Expected allele frequency} = b1*\text{observed frequency} + b2*\text{observed frequency}^2 + b3*\text{observed frequency}^3 + b4*\text{observed frequency}^4 \text{ without intercept.}$$

Either the corrected (Rafk and Rafn) or uncorrected frequencies (Raf) are used as observed frequency in the formula above.

By comparing the expected with the predicted allele frequency from the model the best correction procedure (Rafk, Rafn or Raf) can be found.

The regression coefficients from the best correction procedure can later be used to correct the allele frequencies from the pools of 2 individuals in Step 5a.

Step 4) From the 50 individual samples construct 25 DNA pools of 2 individuals in the ratio 1:3. Note which individual is used once and which one is used 3 times in the pool Step 5a) Correction based on results of pool of 50 individuals.
With the correction factors found in Step 1 (K, AAavg and BBavg) and Step 3 (regression factors b1, b2, b3 and b4) the allele frequencies can be calculated from the resulting signal intensities in the pools, constructed under Step 4. First Raf or Rafk or Rafn is calculated (depending on the best correction procedure found in Step 3) using correction factors K, AAavg and BBavg from Step 1.

Then Rafc or Rafnc or Rafnc is calculated using the polynomial regression coefficients found under Step 3 as Expected allele frequency=$b1$*observed frequency+ $b2$*observed frequency$^2$+$b3$*observed frequency$^3$+$b4$*observed frequency$^4$ where observed frequency=Raf or Rafk or Rafn.

With two individuals in a pool the predicted corrected frequencies should give the result points 0%, 12.5%, 25.0%, 37.5%, 50.0%, 62.5%, 75.0%, 87.5% and 100%. Rounding off should be done to the nearest result point. The genotypes of the two individuals can be derived from the results as indicated in Table 2 of Example 1.

Step 5b) Correction based on results of pools of 2 individuals.

Raf, Rafk and Rafn are calculated based on the signal intensities of the pools constructed under Step 4 and the correction factors K, AAavg and BBavg found under Step 1.

Then polynomial regression coefficients using the same model as in Step 3, Example 5 can be calculated based on 20 pools. This model can be applied on every SNP separately or across all SNPs.

The allele frequencies in the other 5 pools are predicted based on these regression factors as:

Rafkc=$b1$*Rafk+$b2$*Rafk$^2$+$b3$*Rafk$^3$+$b4$*Ra fk$^4$ from regression model with Rafk.

Rafn=$b1$*Rafn+$b2$*Rafn$^2$+$b3$*Rafn$^3$+$b4$*Rafn$^4$ from regression model with Rafn Rafc=$b1$*Raf+$b2$*Raf$^2$+$b3$*Raf$^3$+$b4$*Raf$^4$ from regression model with Raf.

This can be repeated 5 times in such a way that all samples are used for prediction once. The expected allele frequencies in these pools then are compared with the predicted allele frequencies to find the best correction procedure.

With two individuals in a pool the predicted corrected frequencies should give the result points 0%, 12.5%, 25.0%, 37.5%, 50.0%, 62.5%, 75.0%, 87.5% and 1.00%. Rounding off should be done to the nearest result point. The genotypes of the two individuals can be derived from the results as indicated in Table 2 of Example 1.

Step 5c) Correction based on results of pools of 2 individuals.

Another way of prediction can be done using multi linear regression coefficients by SNP on the light intensities (X or Xraw and Y and Yraw) based on the following model
Expected allele frequency=$b1$*$X$+$b2$*$Y$ or Expected allele frequency=b1*Xraw+$b2$*Yraw.

With these multi linear regression factors allele frequencies can then be predicted using Predicted allele frequency=intercept+$b1$*$X$+$b2$*$Y$ or Predicted allele frequency=intercept+$b1$*Xraw+ $b2$*Yraw The multi linear regression coefficients, as describe above, are calculated based on 20 pools.

Then the allele frequencies of the other 5 pools are predicted based on these regression factors. This is repeated 5 times in such a way that all samples are used for prediction once. The expected allele frequencies in these pools then can be compared with the predicted allele frequencies to find the best correction procedure.

As in Step 5a and Step 5b the genotypes of the two individuals can be derived from the results as indicated in Table 2 of Example 1.

Step 6) From other individual samples construct DNA pools of 2 individuals in the ratio 1:3. Note which individual is used once and which one is used 3 times in the pool as in Step 4.

From these pools we can get the genotypes using the best correction method for prediction of the allele frequency as described and using Table 2 of Example 1.

Experiment 1

Application of Procedures Described in Example 5 to Whole-Genome SNP Analysis Using Infinium Assay Beadchip Technology (Illumina, Inc. USA).

Genotyping was done on 50 individuals using the 18K Chicken SNP iSelect Infinium assay (Illumina Inc, USA), with SNPs evenly distributed throughout the chicken genome (van As et al., 2008). Details on the assay, workflow and chip can be found on the website of Illumina.

To check whether frequencies can be estimated accurately, 8 alleles (from 4 different animals out of the 50 individually genotyped individuals) were combined in one pool. Steps 1 to 3 and Step 5, as describe in Example 5, were taken except the translation from predicted allele frequencies into genotypes, using Table 2, was not performed.

In Step 4 equimolar quantities of DNA of 4 individuals were pooled in stead of DNA from 2 individuals in the ratio 1:3.

If ratio 1:3 from 2 different animals is used we can regard this is combining 8 alleles into a pool. By using equimolar quantities of 4 individuals also 8 alleles are combined.

This way 12 pools were composed and one pool of 50 animals as in step 1 (same samples are used as in the pools of 4 plus the 2 extra samples). Then these 13 pools were genotyped using a second batch of infinium chips.

K, AAavg and BBavg per SNP were calculated as in Example 5, Step 1. Then uncorrected and corrected allele frequencies from the pool of 50 were calculated as in Example 5, Step 2.

Also polynomial regression coefficients were calculated as in Example 5, Step 3.

Further more the polynomial and multi linear regression coefficients, as described in Step 5b and 5c, were calculated. This was done based on 11 pools and then allele frequencies in the remaining pool was predicted using the regression factors.

In this experiment the multi linear regression on X and Y (intensities for red and green) gave the best results. For final results see FIG. 4 and Table 9.

In total 4.6% of the allele frequencies were falling in the wrong class. In case these were pools of 2 individuals in a ratio of 1:3 this would have resulted in 3.0% genotyping errors.

TABLE 9

Number of predicted allele frequencies by class compared to the expected allele frequencies. The numbers on the diagonal will lead to correct genotypes. The allele frequencies outside the diagonal but within the boxes will result in one genotype error. The other results will end in 2 genotype errors.

| Allele Frequency Expected | Predicted 0 | 12.5 | 25 | 37.5 | 50 | 62.5 | 75 | 87.5 | 100 | Total |
|---|---|---|---|---|---|---|---|---|---|---|
| 0 | 59489 | 144 | 13 | | 2 | | 1 | | | 59649 |
| 12.5 | 331 | 12888 | 452 | 11 | 3 | 1 | | | | 13687 |
| 25 | 27 | 427 | 12060 | 897 | 10 | 1 | | | | 13422 |
| 37.5 | 2 | | 374 | 11342 | 1026 | 17 | 1 | | | 12762 |
| 50 | | | 4 | 671 | 11590 | 1098 | 27 | | | 13390 |
| 62.5 | 1 | | | 5 | 682 | 11074 | 727 | | 1 | 12490 |
| 75 | | | 1 | | 3 | 779 | 11421 | 494 | 29 | 12727 |
| 87.5 | | | 1 | | 1 | 3 | 528 | 11172 | 416 | 12121 |
| 100 | 10 | | | 3 | 1 | 6 | 5 | 50 | 50896 | 50971 |

Experiment 2

Application of Procedures Described in Example 5 to SNP Analysis Using Veracode Assay Technology (Illumina, Inc. USA).

Genotyping was done on 50 individuals using the 96 Chicken SNP Veracode, Golden Gate Assay (Illumina Inc, USA), with SNPs evenly distributed throughout the chicken genome (Step 1). Details on the assay, workflow and chip can be found on the website of Illumina.

Also 1 pool of all samples was constructed (as in Step 2) and 24 pools of 2 individuals in the ratio 1:3 (as in Step 4). These 25 pools were genotyped with a second batch of chemicals.

All corrections were done as described in Step 1 to 3 of Example 5.

The correction in Step 5a was applied on all 24 pools of 2 using the polynomial regression factors found in Step 3.

For Step 5b and Step 5c we used 23 pools every time to calculate the regression factors (polynomial in Step 5b and multi linear in Step 5c) to be able to predict the allele frequencies for the remaining pool. In total we did this 24 times so all pools were used once to predict the allele frequencies.

The best results were obtained using Rafk (calculated on base of normalised values X and Y) and then corrected using the polynomial regression factors from Step 5b resulting in Rafkc.

In total 84 SNPs were called in the individuals. Then some SNPs were not called on some of the individuals. In total we had 1906 complete combinations of pool*SNP.

TABLE 10

Number of predicted allele frequencies by class compared to the expected allele frequencies. The numbers on the diagonal will lead to correct genotypes. The allele frequencies outside the diagonal but within the boxes will result in one genotype error. The other results will end in 2 genotype errors.

| Genotypes Expected | Predicted CC CC | AC CC | AA CC | CC AC | AC C | CC C | AC C | AA AC | CC AA | AC AA | AA AA | Total |
|---|---|---|---|---|---|---|---|---|---|---|---|---|
| CC CC | 312 | 9 | | | | | | | | | | 321 |
| AC CC | 4 | 156 | 4 | | 2 | | | | | | | 166 |
| AA CC | | 13 | 39 | | 7 | 3 | | | | | | 62 |
| CC AC | | | | 10 | 129 | 7 | 1 | | | | | 147 |
| AC AC | | | | | 9 | 228 | 12 | 1 | | | | 250 |
| AA AC | | | | | | 24 | 144 | 5 | | | | 173 |
| CC AA | | | | | | | | 4 | 49 | 9 | | 62 |
| AC AA | | | | | | | | | 7 | 135 | 1 | 143 |
| AA AA | | | | | | | | | 1 | 5 | 576 | 582 |
| Total | 316 | 176 | 54 | 147 | 265 | 159 | 64 | 148 | 577 | | | 1906 |

In total there were 138 (138/1906*100=7.2%) mismatches (Table 10). Because every observation consists of 2 individual samples this resulted in 174 genotype errors (170/1906*2*100=4.46%), see Table 11, FIG. 5 and FIG. 6.

The process of defining the best correction procedure in this example (as done using Step 3 (Example 5) and Step 5a, 5b or 5c (Example 5)) also delivers information about the number of mismatches by SNP. This makes it possible to eliminate a SNP from the set to reduce the risk of mistakes at an expense of lower call rates.

TABLE 11

Number of correctly predicted genotypes

| Expected | Predicted CC CC | AC CC | AA CC | CC AC | AC AC | AA AC | CC AA | AC AA | AA AA | total |
|---|---|---|---|---|---|---|---|---|---|---|
| CC CC | 624 | 9 | | | | | | | | 633 |
| AC CC | 4 | 312 | 4 | 0 | | | | | | 320 |
| AA CC | | 13 | 78 | 0 | 0 | | | | | 91 |
| CC AC | | | 0 | 258 | 7 | 1 | | | | 266 |
| AC AC | | | | 8 | 456 | 12 | 0 | | | 477 |
| AA AC | | | | | 24 | 288 | 0 | | | 312 |
| CC AA | | | | | | 0 | 98 | 9 | | 107 |
| AC AA | | | | | | | 7 | 270 | 1 | 278 |
| AA AA | | | | | | | 1 | 5 | 1152 | 1158 |
| Total | 628 | 331 | 83 | 266 | 491 | 297 | 107 | 282 | 1153 | 3642 |

Experiment 3

Application of Procedures Described in Example 5 to SNP Analysis Using Other Genotyping Methods The procedures described in Example 5 can also be used in any other genotyping method, other than the methods described in Experiment 1 and Experiment 2, such as Affymetrix GeneChip (Affymetrix Inc, USA) or Agilent Technologies.

Example 6

Use of the Invention in Sequencing Protocols as in Example 4 but Using Other Correction Methods Step 1) Perform sequence reactions for 50 individuals separately Use peak height of allele 1 and peak height of allele 2 as the Xraw and Yraw value or the relative peak height as X and Y.
Relative peak height for allele 1 is $X = X/(X+Y)$ and relative peak height for allele 2 is $Y = Y/(X+Y)$.
Then calculate K, AAavg and BBavg the same way as done for genotyping in Step 1 of Example 5;

Step 2) Perform sequence reactions in one pool of all 50 individuals

Calculated uncorrected and corrected allele frequencies as in Step 2 of Example 5;

Step 3) Calculate frequencies from individual sequencing and from the pool Use same model as in Step 3 of Example 5 to find polynomial regression coefficients.

Step 4) Perform sequence reactions for 25 pools of 2 pooled individuals

Step 5a) Compare corrected frequencies with expected frequencies based on the pool of all 50 individuals to find best method.

Step 5b) Calculate Rafnc, Rafkc and Rafc in 5 pools of 2 individuals using the polynomial regression factors found in the other 20 pools using the model Expected allele frequency=$b1$*observed frequency+ $b2$*observed frequency$^2$+$b3$*observed frequency$^3$+$b4$*observed frequency$^4$ without intercept.

Step 5c) Calculate predicted allele frequency in 5 pools of 2 individuals using the multi linear regression coefficients found in the other 20 pools using the model Predicted allele frequency=intercept+$b1$*X+$b2$*Y or Predicted allele frequency=intercept+$b1$*Xraw+ $b2$*Yraw From Step 3 and Step 5 determine the best correction procedure by repeating Step 5b and 5c several times in such a way that all pools are being used for prediction of allele frequencies (validation).

If needed other numbers for validation can be used. E.g. one can use 24 pools for finding the regression factors and then predicting one using these factors. In total one then needs to repeat this 25 times.

With the best correction procedure and the needed correction factors and regression factors it was possible to predict frequencies of new pools and read the resulting alleles in Table 2.

LEGENDS TO THE FIGURES

Figure 1:
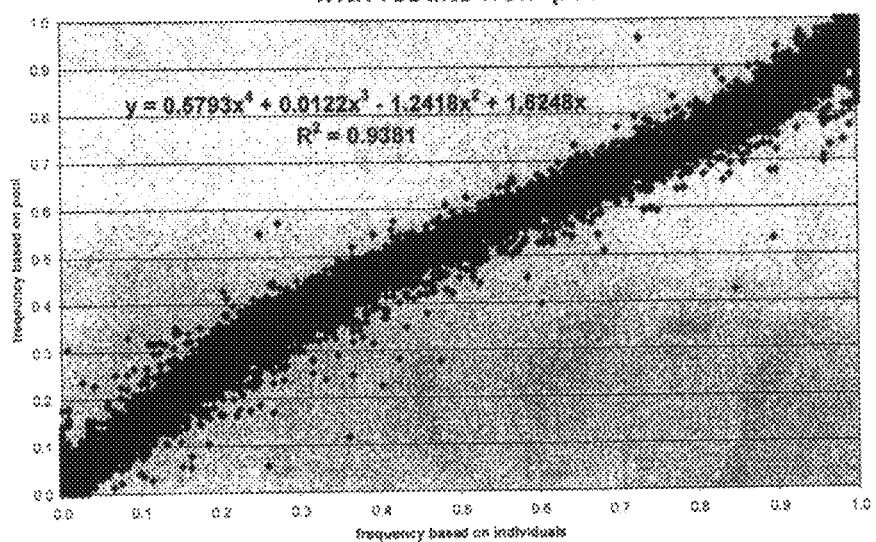
FIG. 1 shows in a graphical display the correlation between the allele frequency as based on pooled data (Y-axis) and the allele frequency as based on individual measurements (X-axis).
Figure 2:
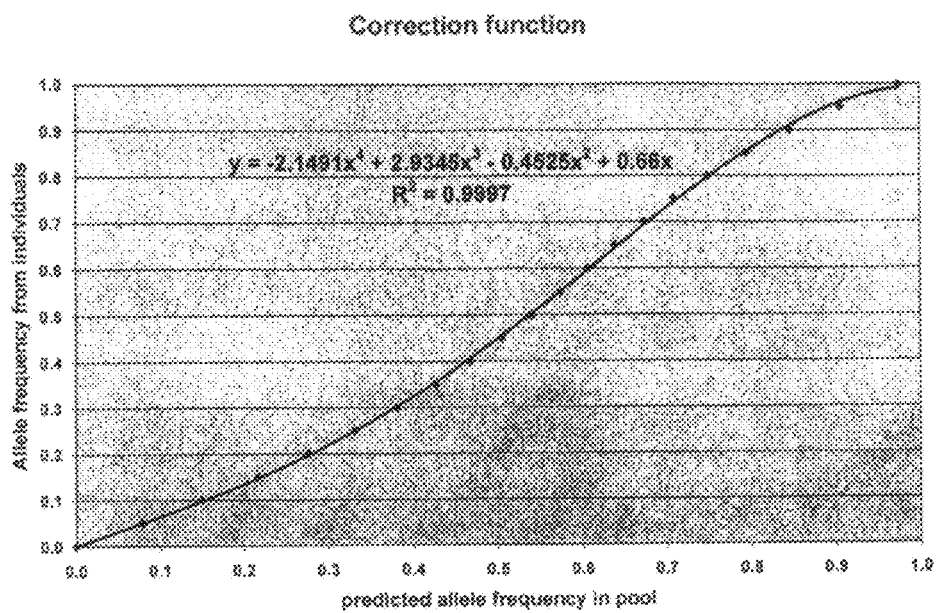
FIG. 2 shows in graphical display the relationship between allele frequency as measured on individuals (Y-axis) and the predicted allele frequencies in pool (X-axis).
Figure 3:
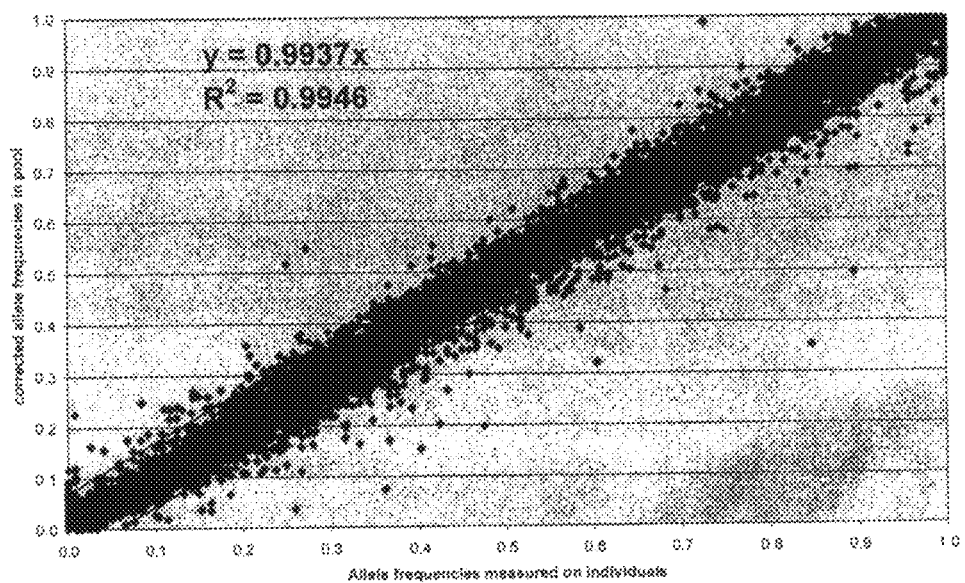
FIG. 3 shows in graphical display the relationship between the corrected allele frequency in the pool (Y-axis) and the allele frequencies measure on individuals after individual typing (X-axis).
Figure 4:
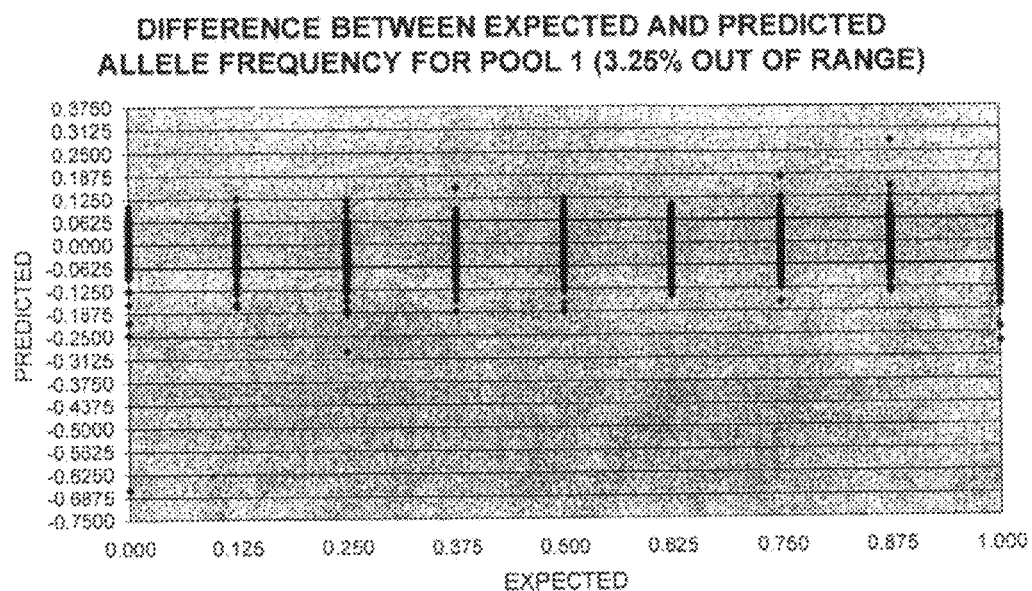
FIG. 4 shows in graphical display the difference between the expected (based on individual typings) and predicted allele frequencies for pool 1 in experiment 1.
Figure 5:
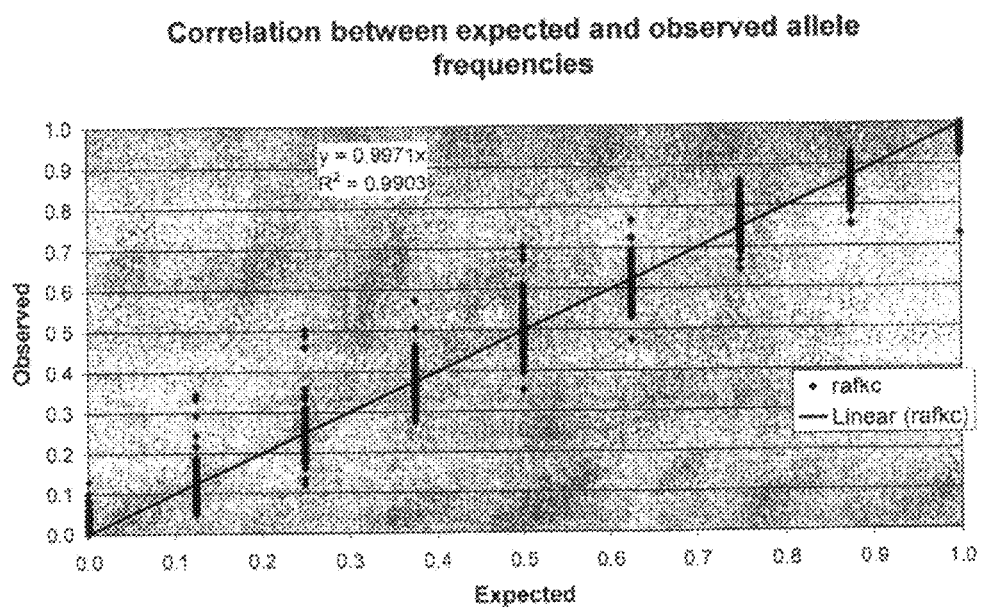
FIG. 5 shows in graphical display the correlation between the expected (based on individual typings) and predicted allele frequencies for all pools in experiment 2.
Figure 6:
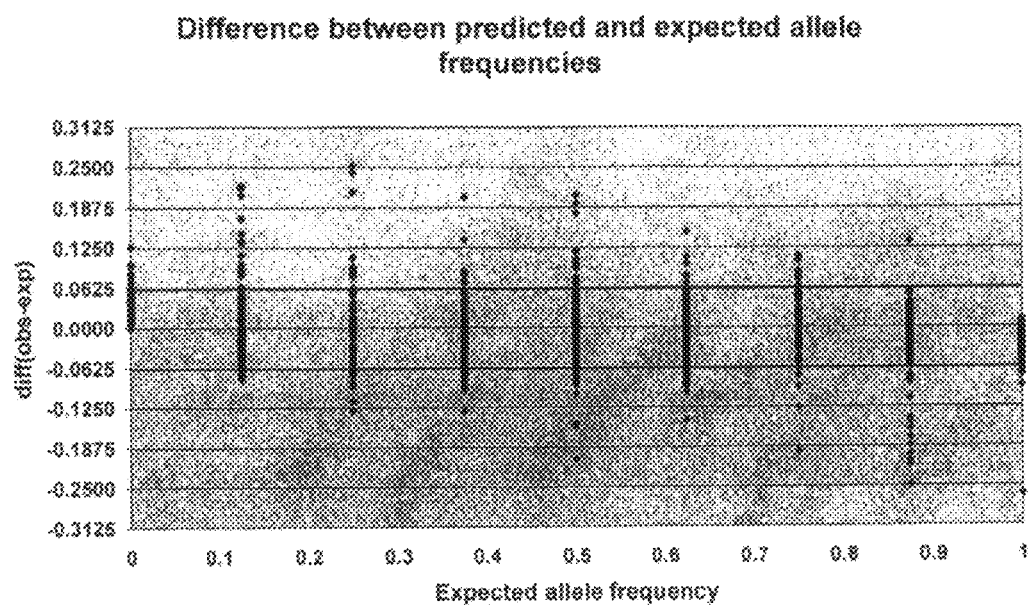
FIG. 6 shows in graphical display the difference between the expected (based on individual typings) and predicted allele frequency for all pools in experiment 2.
Figure 7:
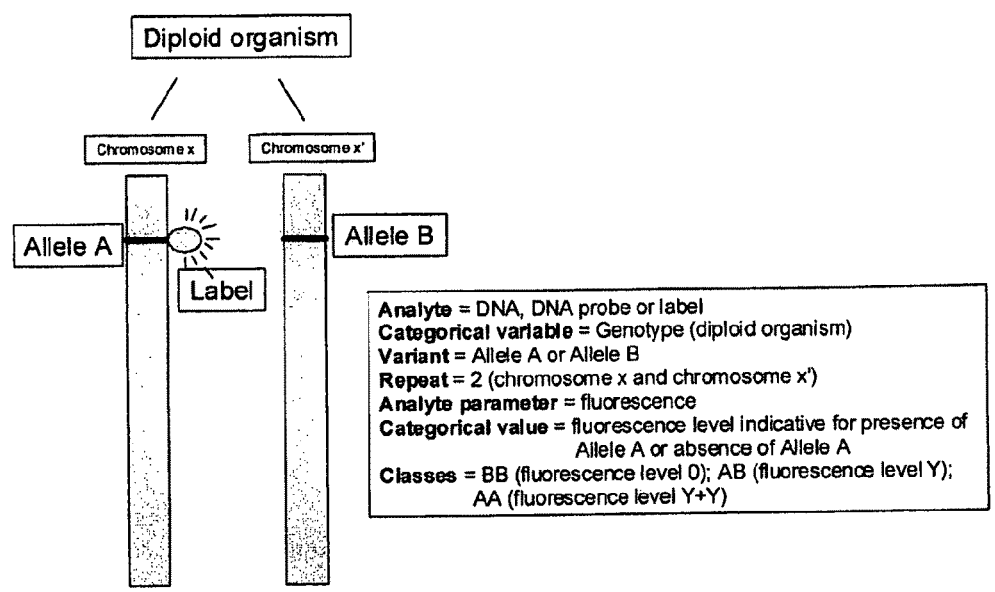

The invention claimed is:
1. A method for genotyping comprising:
a) pooling n individual samples to form a pool of multiple samples wherein the individual samples in the pool are present in a molar ratio of $x^0:x^1:x^2:x^{(n-1)}$, wherein x is equal to a positive value other than 1;
b) quantitatively measuring a signal in the pool, wherein the intensity of the signal relates to the number of alleles present in the pool, and allocating the result of the measurement to one out of y* $((p+1)^0+(p+1)^1+(p+1)^2+(p+1)^{(n-1)})$values, wherein y is the number of potential different alleles, p is the ploidy level, and wherein the lowest value is 0%, being equal to the minimum possible signal strength, the highest is 100%, being equal to the maximum possible signal strength, and the intermediate values are arranged according to equal intervals of $(1/y*((p+1)^0+(p+1)^1+(p+1)^2+(p+1)^{(n-1)}))* 100\%$; and, c) determining the genotype of each individual sample in the pool from the value allocated in b), taking into account the molar ratio at which each individual sample contributed to the pool of multiple samples.

2. The method of claim 1, wherein the genetic marker is a variant of a biomolecule.

3. The method of claim 2, wherein the biomolecule is a variant of a nucleic acid or a variant of a polypeptide.

4. The method of claim 3, wherein the nucleic acid is a nucleotide polymorphism.

5. The method of claims 3, wherein the nucleic acid is quantitatively measured in a sequencing assay.

6. The method of claim 1, wherein the genetic marker is labeled and quantitatively measuring comprises measurement of the intensity, peak height or peak surface of an instrument signal.

7. The method of claim 6, wherein the instrument signal is a fluorescence signal.

8. The method of claim 1, wherein x is equal to p+1 and wherein p represents the ploidy level from which the individual samples are obtained.

9. The method of claim 1, wherein x is 3.

* * * * *